(12) United States Patent
Jehanli et al.

(10) Patent No.: US 7,790,400 B2
(45) Date of Patent: Sep. 7, 2010

(54) DELTA-9-TETRAHYDROCANNABINOL DETECTION METHOD

(75) Inventors: Ahmed Mohammed Taki Jehanli, Abingdon (GB); Christopher William Hand, Abingdon (GB)

(73) Assignee: Concateno UK Limited, Abingdon, Oxfordshire (GB)

(*) Notice: Subject to any disclaimer, the term of this patent is extended or adjusted under 35 U.S.C. 154(b) by 367 days.

(21) Appl. No.: 11/630,583

(22) PCT Filed: Jul. 1, 2005

(86) PCT No.: PCT/GB2005/050099

§ 371 (c)(1),
(2), (4) Date: May 9, 2008

(87) PCT Pub. No.: WO2006/003472

PCT Pub. Date: Jan. 12, 2006

(65) Prior Publication Data

US 2009/0017555 A1 Jan. 15, 2009

(30) Foreign Application Priority Data

Jul. 2, 2004 (GB) .................................. 0414898.7

(51) Int. Cl.
*G01N 33/53* (2006.01)
(52) U.S. Cl. .................... 435/7.1; 435/7.2; 435/7.91; 435/7.92
(58) Field of Classification Search .................. None
See application file for complete search history.

(56) References Cited

U.S. PATENT DOCUMENTS

| | | |
|---|---|---|
| 3,996,344 A | 12/1976 | Gross |
| 4,016,146 A | 4/1977 | Soares |
| 4,041,076 A | 8/1977 | Avenia et al. |
| 4,067,774 A | 1/1978 | Rubenstein et al. |
| 4,329,281 A | 5/1982 | Christenson et al. |
| 4,771,005 A | 9/1988 | Spiro et al. |
| 4,843,020 A | 6/1989 | Woodford et al. |
| 5,248,791 A | 9/1993 | Brynes et al. |
| 5,279,955 A | 1/1994 | Pegg et al. |
| 5,677,132 A | 10/1997 | Strahilevitz et al. |
| 6,326,159 B1 | 12/2001 | Ullman et al. |
| 2003/0207469 A1 | 11/2003 | Rouhani et al. |
| 2008/0286816 A1 | 11/2008 | Jehanli |

FOREIGN PATENT DOCUMENTS

| | | |
|---|---|---|
| CN | 1140770 A | 4/2003 |
| EP | 0 279 213 | 8/1988 |
| EP | 0 359 063 | 3/1990 |
| EP | 0 371 253 | 6/1990 |
| EP | 0 560 411 | 9/1993 |
| EP | 1 167 976 | 1/2002 |
| EP | 1 178 316 | 2/2002 |
| EP | 0 560 410 | 10/2002 |
| EP | 0 291 194 | 7/2003 |
| EP | 1 340 981 | 9/2003 |
| GB | 2 339 615 | 2/2000 |
| GB | 2404023 | 1/2005 |
| GB | 2 404 022 | 1/2006 |
| WO | WO 00/04381 | 1/2000 |
| WO | WO 02/057739 | 7/2002 |
| WO | WO 2005/090987 | 9/2005 |
| WO | WO 2005/121793 | 12/2005 |

OTHER PUBLICATIONS

International Search Report for PCT/GB2005/050099, mailed on Dec. 16, 2005, 3 pages.
Jehanli et al., Journal of Forensic Sciences (2001) 46(5):1214-1220.
Braithwaite et al. (1995) "Screening for Drugs of Abuse. I: Opiates, Amphetamines and Cocaine" Annals of Clinical Biochemistry 32:123-153.
Pichini et al. (1996) "Drug Monitoring in Nonconventional Biological Fluids and Matrices" Clinical Pharmacokinetics 30:211-228.
Rollins et al. (1997) "Testing for Drugs of Abuse in Hair—Experimental Observations and Indications for Future Research" Forensic Science Review 9:23-25.
Stout et al. (2003) "Comparison and Evaluation of DRI® Methamphetamine, DRI Ecstasy, Abuscreen® ONLINE Amphetamine, and a Modified Abuscreen ONLINE Amphetamine Screening Immunoassays for the Detection of Amphetamine (AMP), Methamphetamine (MTH), 3,4-Methylenedioxyamphetamine (MDA), and 3,4-Methylenedioxymethamphetamine (MDMA) in Human Urine*" Journal of Analytical Toxicology 27:265-269.
Stout et al. (2004) "Evaluation of Ephedrine, Pseudoephedrine and Phenylpropanolamine Concentrations in Human Urine Samples and a Comparison of the Specificity of DRI® Amphetamines and Abuscreen® Online (KIMS) Amphetamines Screening Immunoassays*" Journal of Forensic Sciences 49:160-164.

*Primary Examiner*—Jacob Cheu
(74) *Attorney, Agent, or Firm*—Swanson & Bratschun, L.L.C.

(57) ABSTRACT

The invention provides competitive immunoassay techniques for high sensitivity detection of delta-9-tetrahydro-cannabinol (*cannabis*; THC) employing a carrier conjugate of an intermediate in the biosynthesis of *cannabis*, more particularly 5-pentylresorcinol conjugated to a macromolecular carrier via its hydroxyl groups. By employing such a conjugate with anti-THC antibody in a lateral flow immunochromatography test device convenient on-site testing for low levels of *cannabis* in liquid samples may be achieved. Such testing is particularly favoured for roadside testing for *cannabis* in oral fluid samples.

28 Claims, 5 Drawing Sheets

Delta-9-THC 11-nor-9-carboxy-delta-9-Tetrahydrocannabinol
(THC-COOH)

11-Hydroxy-delta-9-THC

DELTA-9-TETRAHYDROCANNABINOL DETECTION METHOD

CROSS-REFERENCE TO RELATED APPLICATIONS

This application is the national phase of PCT application PCT/GB2005/050099 having an international filing date of Jul. 1, 2005, which claims priority from British application number 0414898.7 filed Jul. 2, 2004. The contents of these documents are incorporated herein by reference.

The invention relates to competitive immunoassay techniques for the detection of cannabinoids, especially delta-9-tetrahydrocannabinol (*cannabis*; THC) and related metabolites, in biological matrices, environmental compositions and at surfaces. In particular, the invention provides procedures for high sensitivity detection of THC in devices for use in point-of-care and on-site testing.

BACKGROUND OF THE INVENTION

*Cannabis* is today the most widely abused illicit drug in the world (Journal of Chromatography B, volume 733, pages 119-126) and in many countries it is assigned as a class 1 or class 2 prohibited drug. The detection of cannabinoids is routinely carried out by forensic scientists, toxicologists, drug rehabilitation clinics and as part of workplace testing for drugs of abuse. Recently, it has become a major illicit drug targeted for driving under the influence testing.

Delta-9-tetrahydrocannabinol (THC, see structural diagram I in FIG. 1) is the primary psychoactive analyte in the flowering or fruity tops, leaves and resin of the plant *Cannabis sativa*. THC is extensively metabolised in man to two main products, 11-nor-9-carboxy-delta-9-THC (THC-COOH, see structural diagram II in FIG. 1) and 11-hydroxy-delta-9-THC (THC-OH, see structural diagram III in FIG. 1). Of these two metabolites, only the hydroxy metabolite has psychoactive effects.

Known THC detection methods, and known *cannabis* detection methods in general, can be classified into three groups. The gold standard techniques employ GS/MS, tandem GC/MS/MS, LC/MS and tandem LC/MS/MS (GC=gas chromatography; LC=liquid chromatography; MS=mass spectrophotometry). These techniques are strictly laboratory based and require specialist training and equipment, which renders them unsuitable for point-of-care testing.

Qualitative methods for *cannabis* detection are also known in the prior art. U.S. Pat. Nos. 3,715,189, 4,196,167, 4,771,005, 4,816,415 and 5,457,054, and also GB Patent no. 1426177 and references within, describe methods for *cannabis* detection based on chemical reactions involving colour change. However, chemical methods tend to be non-specific and lack the sensitivity level required for the detection of drugs in biological matrices.

The third group of known cannabinoid detection methods employ immunological techniques. For example, antibodies are raised to various cannabinoid derivatives conjugated to a carrier macromolecule and immunoassays are then set up using these antibodies and labelled derivatives thereof, e.g., radiolabelled or fluorescent derivatives for use in radioimmunoassays and fluoroimmunoassays and enzyme-labelled derivatives for use in various formats of enzyme immunoassay. Such enzyme immunoassays include, for example, direct ELISAs using immobilised drug derivative and enzyme-labelled antibody. As an alternative format, labelled anti-cannabinoid antibodies, e.g. such antibodies labelled with latex particles or colloidal gold, have been used for cannabinoid detection by lateral flow immunochromatography. The drug derivatives used are generally based upon the parent molecule delta-9-tetrahydrocannabinol (THC) and its major metabolite THC-COOH. For THC modification, a cross-linking reagent is normally attached to the compound at the C2, C5' or the phenolic group C1 position (see for example patents GB1364925, EP0276732, EP0279308, U.S. Pat. No. 5,237,057, U.S. Pat. No. 5,747,352 and Nature New Biology (1972) volume 236 pages 216-217). THC-COOH can also be derivatised in the same manner as THC. In addition, the availability of the carboxylic group at C9 of THC-COOH allows direct cross-linking to the amino groups of carrier molecules using the carbodiimide coupling reaction. Antibodies raised to THC or THC-COOH coupled via the C1, C2 and C5' are expected to show different cross-reactivity for those two compounds due to the absence and presence of the carboxylic group at C9, respectively. Therefore, to achieve comparable cross-reactivity for THC and THC-COOH, many of the known immunoassays for detection of those compounds employ antibodies raised to THC-COOH coupled to a carrier molecule via the carboxylic group at C9.

Many immunoassays for THC are commercially available. The Roche Diagnostics radioimmunoassay (U.S. Pat. No. 4,438,207) and fluorescence polarisation immunoassay (European Patent no. 0392332) use antibodies raised to THC-COOH coupled to a carrier protein via the phenolic group at C1 and a similarly radiolabelled or fluorescence labelled THC-COOH. As expected, this assay shows excellent detection of the acid but only 5% cross-reactivity with the parent drug, THC. Abbott's fluorescence polarization immunoassay (European Patent no. 0279308) uses antibodies raised to THC-COOH linked to a carrier protein via the carboxylate group at C9 and THC-COOH with a fluorescent moiety at the same position. This assay shows a better cross-reactivity with the parent drug as well as the 11-hydroxy derivative (FIG. 1, compound III). A number of enzyme immunoassays for cannabinoid detection are also available including one made available by Cozart Bioscience Limited. These employ an antibody raised to THC-COOH linked to a carrier protein via the carboxylate group and horseradish peroxidase (HRP)-labelled THC-COOH (label attached via the carboxylate group of the acid).

Almost all of the described immunoassays are good for detecting THC-COOH making them suitable for the detection of *cannabis* use using matrices like urine and blood. However, oral fluid (saliva) from *cannabis* users shows no or minute amounts of THC-COOH and THC-OH. Determination of the primary psychoactive component, THC, is thus essential in the case of roadside testing for driving under the influence of that drug using oral fluid samples (proposed as the best matrix for roadside testing for drugs of abuse). The ability to detect low amounts of the parent drug THC is also necessary to be able to pick up recent use of this drug. The present invention addresses this problem by providing new competitive immunoassay techniques for THC detection, which may also provide the advantage of exhibiting high cross-reactivity for both THC-COOH and THC-OH.

SUMMARY OF THE INVENTION

It has now been found that by using a carrier conjugate of an intermediate in the biosynthesis of THC, more particularly 5-pentylresorcinol (see FIG. 2) conjugated to a macromolecular carrier such as bovine serum albumin via its hydroxyl groups, THC can be detected by competitive immunoassay at even very low levels, e.g. $\leq$20 ng/ml, as may be found in oral fluid samples. Unexpectedly, it was found that 5-pentylresorcinol in free solution does not interfere with the binding of commercially available anti-THC antibody (mouse monoclonal anti-THC antibody as available from East Coast Biologics, USA) to immobilised 5-pentylresorcinol-macromolecule conjugates. Furthermore, THC-OH can be detected using such a conjugate and antibody combination at comparable sensitivity to the parent drug while THC-COOH can be detected at far higher sensitivity, as low as about 1.0 ng/ml.

Accordingly, the invention provides in one aspect a method for detecting in a liquid sample THC, which comprises:

(a) contacting said sample with (i) a 5-pentylresorcinol/macromolecular carrier conjugate wherein 5-pentylresorcinol is conjugated via a hydroxyl group or derivative thereof on its benzene ring to the carrier and (ii) an anti-THC antibody which is capable of binding both THC and said conjugate; and (b) determining whether the binding of said antibody to said conjugate is reduced in the presence of said sample.

Desirably, the anti-THC antibody will additionally bind both THC-COOH and THC-OH, e.g. an antibody will be employed raised to THC-COOH coupled to a carrier protein via the carboxylate group as exemplified by the commercial anti-THC antibody noted above. A reduction in binding of the antibody to conjugate in a method of the invention will then be indicative that the sample contains one or more of THC, THC-COOH and THC-OH at equal to or greater than the minimum detectable level.

An assay method of the invention may conform with any conventional format for a competitive immunoassay. It may, for example, take the format of a conventional competitive ELISA in which the antibody or the 5-pentylresorcinol/carrier conjugate is immobilised on a solid support. However, most conveniently for on-site testing, e.g. roadside testing, a method of the invention may take the form of a lateral flow immunochromatography assay employing a porous test strip. In this case again, the immobilised reagent for analyte detection may be immobilised antibody or immobilised 5-pentylresorcinol/carrier conjugate.

In a further aspect, the invention also provides kits for a carrying out an immunoassay of the invention comprising (i) a 5-pentylresorcinol/carrier conjugate as described above and (ii) an antibody capable of binding both said conjugate and THC, more preferably all of THC, THC-COOH and THC-OH.

In still further aspects, the invention provides 5-pentylresorcinol conjugated to a carrier via a hydroxyl group or a derivative thereof on its benzene ring such that it is capable of binding antibody which also binds all of THC, THC-COOH and THC-OH, such a conjugate which is labelled or immobilised on a solid support, methods of making such conjugates and use of such conjugates as an immunogen for antibody production.

DETAILED DESCRIPTION

5-Pentylresorcinol Conjugates

Suitable 5-pentylresorcinol conjugates for use in carrying out assays according to the invention are any such conjugate wherein 5-pentylresorcinol is linked via a hydroxyl group to a macromolecular carrier such that it capable of binding antibody which binds all of THC, THC-COOH and THC-OH. As indicated above, this may be an antibody obtained by using as the immunogen THC-COOH linked to a carrier protein via its carboxylate group as exemplified by the commercial mouse monoclonal anti-THC antibody already mentioned above.

Figure 1:
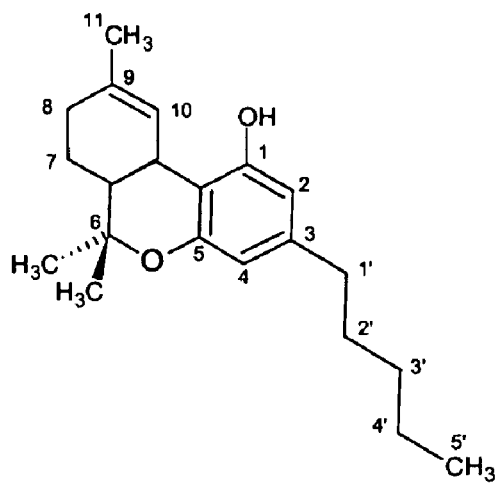
FIG. 1: structural diagrams of THC (I), THC-COOH (II) and THC-OH (III)
Figure 1:
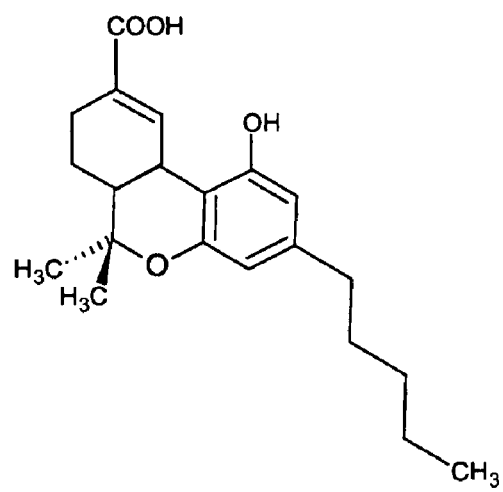
Figure 1:
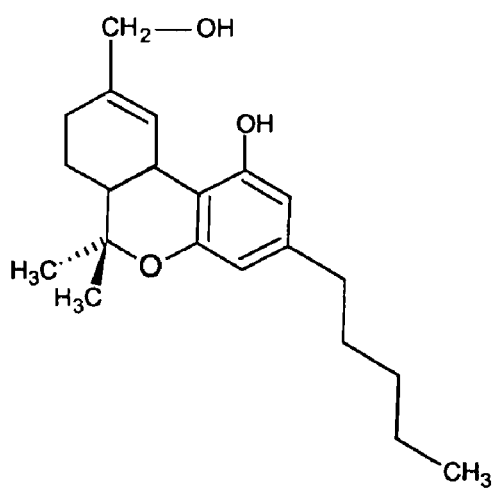
Figure 2:
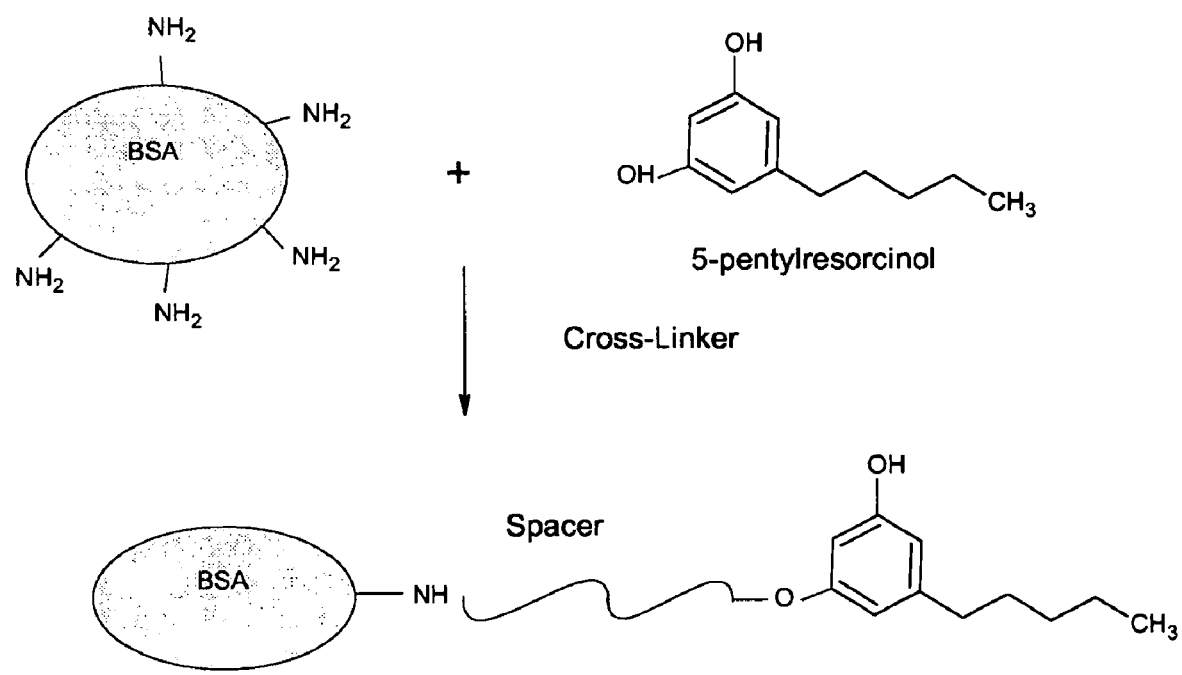
FIG. 2: structural diagram of 5-pentylresorcinol and illustration of coupling of that compound to bovine serum albumin (BSA) via a hydroxyl group.

It will be appreciated that conjugation of 5-pentylresorcinol to the chosen carrier may be via either of the two hydroxyl groups on its benzene ring and conjugate preparations may be employed which contain a mixture of such conjugates which can be expected to be functionally equivalent in an assay of the invention. (Drawing a line across the 5-pentylresorcinol structure as shown in FIG. 2 through the aliphatic side chain and the benzene ring produces two symmetrical halves with the two OH groups being identical). However, it is also envisaged that for the purpose of carrier coupling a hydroxyl group of 5-pentylresorcinol may be derivatised, more particularly, for example, converted to a carboxylate group. In this case, coupling to the carrier may be by the known carbodiimide method.

In one embodiment, the carrier may be a protein. For the purpose of the exemplification, it was found convenient to use bovine serum albumin (BSA), but other proteins may be employed such as ovalbumin, gamma globulins and thyroglobulin. A suitable carrier protein may be an enzyme, for example, horseradish peroxidase. In this case, it is envisaged that the carrier may also serve as a detectable label in an assay of the invention. It is also envisaged that the carrier linked to 5-pentylresorcinol may be a homo- or hetero-polymer containing amino acid side chains such as polylysine, polyornithine or poly-(glutamine, lysine).

The 5-pentylresorcinol conjugate may also be labelled directly or indirectly with a detectable label which is not the carrier. In this case, the label may be joined to any portion of the conjugate whereby the ability to bind suitable antibodies is retained, e.g. a carrier protein. Suitable labels, include, for example, radioisotopes such as $^{125}I$, $^{32}P$ or $^{35}S$, particulate labels such as colloidal gold, latex beads or liposomes, fluorescent labels such as fluorescein, and biotin.

For the purpose of the exemplification, 5-pentylresorcinol was directly linked to a carrier using a cross-linking reagent. Two such approaches are described below, use of the dimethyl aminopyridine/disuccinimidyl carbonate procedure or use of vinyl sulfone. However, other methods known for attaching hydroxyl groups to amino groups are known and may be found equally suitable (for review see "Bioconjugate Techniques" by G. T. Hermanson, 1996, Academic Press). In forming a suitable 5-pentylresorcinol conjugate, a spacer molecule may be employed, e.g. an aminocaproic acid spacer.

Antibodies

As indicated above, a suitable antibody for use in a method of the invention will be capable of specifically binding to a 5-pentylresorcinol conjugate as described above and will also be capable of specifically binding to THC. Desirably, the antibody employed will be capable of specifically binding additionally both THC-COOH and THC-OH. Most desirably, the antibody will show about at least equal or higher cross-reactivity with these two metabolites in a lateral flow immunochromatatography test employing immobilised 5-pentylresorcinol conjugate as exemplified below. Desirably, such an antibody will be capable of detecting THC in such a test at ≦20 ng/ml. While a commercially available antibody for this purpose has already been mentioned above, it will be appreciated that other equally suitable antibodies (polyclonal or monoclonal) may be produced using conventional techniques and THC-COOH coupled via its carboxylate group to a carrier protein, or other THC derivatives bound to a carrier molecule, as the immunogen.

It is envisaged that suitable antibodies may also be generated by using as the immunogen a 5-pentylresorcinol conjugate as described above. It is postulated that linkage of 5-pentylresorcinol to a protein such as BSA via its hydroxyl groups causes change in configuration of the compound in such a way that anti-THC antibodies can specifically recognise the configuration.

An antibody for use in a method of the invention may be labelled directly or indirectly, e.g. by means of secondary labelled antibodies. Suitable labels for this purpose are any label conventionally employed in immunoassays including radioactive labels, fluorescent labels, particulate labels such as colloidal gold, enzyme labels such as horseradish peroxidase and biotin.

The term "antibody" as used herein will be understood to extend to antibody fragments, e.g. Fab, Fab' and Fv fragments, which retain antibody binding capability and might be utilised in a method of the invention.

Competitive Assays

As also indicated above, a method of the invention may adopt any format for performing a competitive immunoassay. Drug-antibody binding may occur in solution followed by separation of bound complexed label. Alternatively and preferably, one of anti-THC antibody and 5-pentylresorcinol conjugate may be bound to a solid support, e.g. a solid support comprising nitrocellulose or plastic, e.g. a plastic well surface, or solid beads, e.g. plastic or glass beads. A method of the invention may thus, for example, conform with a conventional competitive ELISA format employing either directly or indirectly labelled anti-THC antibody or 5-pentylresorcinol/carrier conjugate. In this case, either 5-pentyl resorcinol/carrier conjugate or anti-THC antibody may be immobilised in wells of a microtitre plate or on solid beads. However, alternatively anti-THC antibody or 5-pentylresorcinol/carrier conjugate may be immobilised on a porous test strip or sheet to enable convenient on-site drug testing by a lateral flow immunochromatography assay, e.g. a test strip or sheet comprising nitrocellulose. Such a test strip or sheet may be, for example, in the form of nitrocellulose bound to a backing support, e.g. plastic sheet. Such a test strip or sheet may be nitrocellulose card. Preferred lateral flow immunochromatography tests according to the invention are discussed more fully immediately below and illustrated by the exemplification.

Lateral Flow Methods

Lateral flow immunochromatography tests according to the invention can be carried out using any known form of lateral flow device and relying on competitive anti-cannabinoid antibody binding for analyte detection. Such tests may be carried out using the methodology as described in GB Patent 2339615 of Cozart Bioscience Limited, corresponding published International Application WO 00/04831 and Journal of Forensic Science 2001, volume 46, pages 1214-1220.

A common feature of lateral flow devices for analyte detection is the provision of a test strip or sheet comprising a dry porous material such as nitrocellulose through which a liquid sample can be drawn to reach one or more spatially distinct analyte detection zones. Each such zone presents an immobilised specific binding reagent. For the purpose of a lateral flow immunochromatography test according to the invention, at least one such analyte detection zone will be provided which presents either a suitable 5-pentylresorcinol/carrier conjugate or a suitable anti-cannabinoid antibody. Such a test strip or sheet will also have joined thereto, or integral thereto, a label release zone which is capable of releasing into liquid drawn into that zone either labelled antibody, if said analyte detection zone presents immobilized conjugate or detectable conjugate if said analyte detection zone presents immobilised anti-cannabinoid antibodies.

Thus, there is also provided by the invention a test strip or sheet for carrying out a lateral flow immunochromatography test according to the invention having the following features:

(i) a strip or sheet comprising a dry porous material, preferably nitrocellulose, having immobilised thereon in an analyte detection zone a suitable 5-pentylresorcinol/carrier conjugate as described above or a suitable anti-THC antibody; and (ii) joined to, or integral to, said strip or sheet providing said analyte detection zone a separate label release zone which is capable of releasing into liquid drawn into that zone either said antibody in labelled form, if said analyte detection zone presents immobilised 5-pentylresorcinol conjugate, or, if said analyte detection zone presents immobilised antibody, detectable 5-pentylresorcinol conjugate as previously described. Such detectable conjugate may be, for example, 5-pentylresorcinol conjugate labelled with gold or coloured latex beads.

The exemplification describes in more detail lateral flow immunochromatography according to the invention employing immobilised 5-pentylresorcinol conjugate and labelled anti-THC antibody, more particularly labelled antibody capable of binding THC and exhibiting high cross-reactivity with both THC-COOH and THC-OH. Illustrated is preferred use of gold particle labelled antibody, although other labels may be employed, e.g. again coloured latex particles. Using this methodology and gold-labelled commercially available anti-THC antibody as discussed above, both THC and THC-OH were found to be detectable at ≦20 ng/ml, while THC-COOH was detectable with still greater sensitivity (about 1.0 ng/ml).

In addition to an analyte detection zone as described above, a test strip or sheet for lateral flow tests according to the invention may also have one or more further analyte detection zones for detection of one or more further drugs or drug classes or groups.

It will be appreciated that in a lateral flow device, the label release zone will be proximal to the analyte detection zone(s) having regard to the direction of liquid flow. It may be in the form of pad, e.g. a pad comprising glass fibre, joined to a strip or sheet providing the analyte detection zone(s). Methods for providing in such a strip or sheet an integral label release zone are also well known. For example, a region of a nitrocellulose strip may be glazed, e.g. by depositing an aqueous sugar or cellulose solution and the thus glazed region contacted with the labelled reagent (see, for example, European Patent no. 0291194 and the related European Patents 0560410 and 0560411).

A test strip or sheet for use in a lateral flow method of the invention may also further comprise a sample receiving member or pad proximal to the label release zone. Such a sample receiving member or pad may be made from any bibulous material capable of absorbing liquid rapidly.

Typically, such a test strip or sheet will have, beyond the analyte detection zone(s) in the direction of intended liquid flow along the strip, i.e. distal to the analyte detection zone(s), a further detection zone presenting an immobilised specific binding reagent so as to provide a control zone. The control zone functions to indicate that the liquid of the sample has traversed the preceding analyte detection zone(s) under conditions suitable for analyte detection. For example, where labelled antibody is provided by the label release zone, the control zone may present an immobilised antibody that is capable of binding the labelled antibody.

Distal to the detection zones in the direction of intended liquid flow, a test strip or sheet of the invention may further comprise an absorbent waste pad (end or wicking pad).

The invention also extends to lateral flow reading devices incorporating a test strip or sheet for carrying out a method of the invention, e.g. a portable screening device as described in WO 00/04381 of Cozart Bioscience Limited.

Samples

Suitable test samples will be in liquid form to allow interaction with the anti-cannabinoid antibody. As indicated above, the methodology of the invention is particularly favoured for application to oral fluid (saliva) samples, which may first be diluted with buffer, e.g. Cozart Oral Fluid Dilution Buffer (Cozart Bioscience product CR-BUFF). Such samples are especially favoured for on-site testing, e.g. roadside testing, for *cannabis* using a visual read test or employing a portable lateral flow reading device as described above. However, it will be appreciated that methods of the invention may be applied to any type of liquid sample commonly employed for testing for drugs of abuse. Thus, the sample may be a fluid sample consisting of, or derived from, any of oral fluid, urine, blood, ocular fluid, sweat or hair. A suitable sample may be derived from an environmental source or swab, e.g. a swab contacted with oral fluid in the mouth or a surface suspected of *cannabis* contamination. The sample may be obtained by dissolving a material, e.g. solid resin or powder, to be tested for the presence of *cannabis* in buffer solution. References which may be referred to for sample preparation include "Drug Monitoring in Nonconventional Biological Fluids and Matrices" in Clinical Pharmacokinetics 1996, volume 30, pages 211-228 and "Testing for drugs of Abuse in Hair" in Forensic Science review 1997, volume 9, pages 23-25.

Kits

As previously noted above, the invention additionally extends to kits for carrying out a method of the invention comprising a suitable 5-pentylresorcinol/macromolecular carrier conjugate as described above and an anti-THC antibody. Either the 5-pentylresorcinol conjugate or the anti-THC antibody may be directly labelled with a detectable label. In the case of the 5-pentylresorcinol conjugate, as already indicated above, it may be possible for the carrier part of the conjugate to serve as a detectable label. Alternatively, means for indirectly labelling either the conjugate or anti-THC antibody may be provided, e.g. secondary labelled antibody. Either the 5-pentylresorcinol conjugate or the anti-THC antibody may be immobilised on a solid support. For example, the kit may comprise either the conjugate or the anti-THC antibody immobilised on a test strip or sheet as described above for carrying out lateral flow immunochromatography. Such a test strip or sheet may be inserted into a housing providing a window or windows over the analyte detection zone(s) or together with such a housing.

A kit of the invention may comprise further components. For example, where the test sample is to be collected from a test subject, the kit may further comprise a fluid collection means. e.g. an oral fluid collection device or swab, a vessel such as a vessel suitable for collection of blood or urine. A kit for use in lateral flow method may include a portable reading device into which a housing as described above may be fitted for detection of bound label in the detection zone(s) and digital display of the results.

The following example illustrates the invention.

EXAMPLE

I. Preparation of Bovine Serum Albumin-THC (BSA-THC) Conjugate

THC-COOH was conjugated to BSA using the carbodiimide coupling procedure. The carboxylic acid group of the drug was linked to the side-chain-amino groups of lysine residues as follows:

1. Dissolve 5.0 mg of delta 9-THC acid (Helena, Cat no. DR021) in 1 ml of ethanol.
2. Add 1.0 ml of dimethylformamide (DMF).
3. Add 10 µl of N-methylmorpholine (NMM, Sigma Co., Cat. No. 67869)
4. Add N-hydroxysuccinimide (N-HS), 6.3 mg in 50 µl of dimethylformamide (DMF). Stir mixture in the dark at room temperature for 24 hours.
5. Weigh out 30 mg of bovine serum albumin in a brown bottle. Dissolve in 4 ml of 0.1 M sodium bicarbonate.
6. Add the activated drug drop-wise to the BSA solution. Stir overnight at room temperature in the dark.
7. Add 100 µl of 2 M Tris and keep stirring for another 60 minutes.
8. Dialyse overnight vs. phosphate buffered saline, pH 7.3 containing 0.1% sodium azide.
9. Determine the protein concentration using the Lowry protein assay and adjust to 1 mg/ml in PBS/azide. Store aliquots at −20° C.

Figure 3:
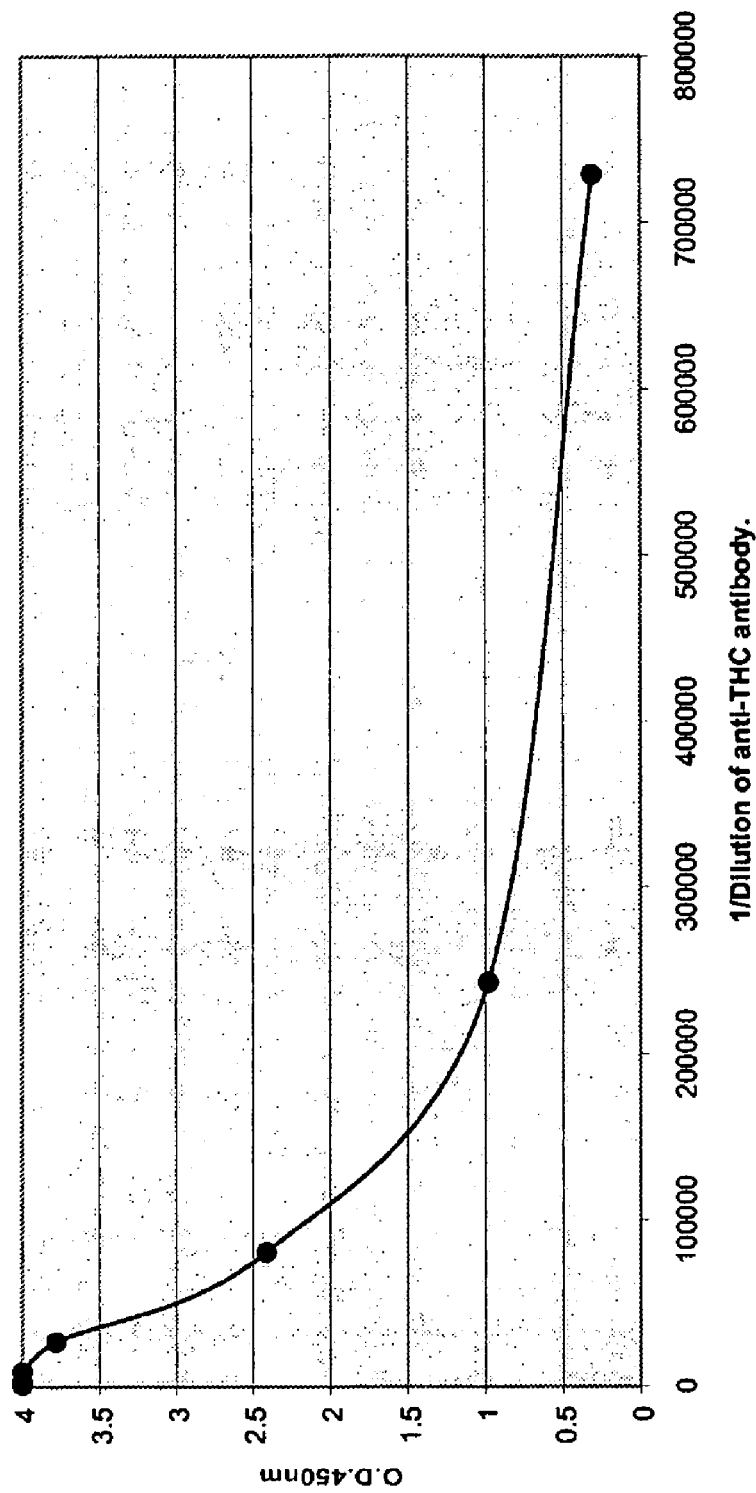
FIG. 3: titration curve for binding of anti-THC antibody to immobilised THC-COOH/BSA conjugate obtained using the carbodimide coupling procedure.

The conjugate was tested by enzyme immunoassay. 96-well microtitre plates were coated, overnight at room temperature, with the conjugate at 5 µg/ml, 100 µl/well in 50 mM sodium carbonate/bicarbonate buffer, pH 9.6. The wells were washed with phosphate buffered saline, pH 7.4 containing 0.05% Tween-20 (Wash buffer) (4 times, 330 µl/well) and blocked in the same buffer for 30 minutes. 3-fold dilutions of mouse monoclonal anti-THC antibody (East Coast Biologics, USA) were added to the wells (100 µl/well) in wash buffer containing 5 mg/ml BSA (assay buffer). After 1 hour incubation at room temperature, the plate was washed 4 times as before with wash buffer and horseradish peroxidase labelled goat anti-mouse IgG was added in assay buffer (1/2000 dilution, 100 µl/well) and the plate incubated for a further 30 minutes. The plate was then washed as before and the substrate solution tetramethylbenzidine was added to the wells (100 µl/well). Colour development was terminated after 30 minutes by the addition of 1 M sulphuric acid (100 µl/well) and the optical density read at 450 nm. FIG. 3 shows a typical titration curve.

II. Preparation of Bovine Serum Albumin-5-Pentylresorcinol Conjugate (BSA-CAN)

5-Pentylresorcinol was coupled to bovine serum albumin via its hydroxyl groups using the dimethyl aminopyridine (DMAP)/disuccinimidyl carbonate (DSC) procedure or vinyl sulfone as follows:

(i) Coupling Using Dimethyl Aminopyridine/Disuccinimidyl Carbonate:

1. Dissolve 10 mg of 5-pentylresorcinol in 1 ml of isopropanol.
2. Dissolve 88 mg of DSC in 0.4 ml DMF.
3. Dissolve 42 mg of DMAP in 0.4 ml of acetone.
4. Add DSC solution drop wise to the 5-pentylresorcinol solution.
5. Add DMAP solution slowly and drop-wise. Stir in the dark overnight at room temperature.
6. Add the activated drug to 70 mg of BSA in 4 ml of 0.1 M sodium bicarbonate. Stir overnight at room temperature.
7. Dialyse the conjugate for three days with three changes of 1 litre each vs. phosphate buffered saline (PBS), pH 7.3 containing 0.1% sodium azide.
8. Determine the protein concentration using the Lowry protein assay and adjust to 1 mg/ml. Store aliquots at −20° C.

Replacing BSA in this procedure by BSA with an aminocaproic spacer gives an equally suitable conjugate.

(ii) Coupling Using Vinyl Sulfone:

1. Dissolve 10 mg of BSA in 1 ml of 0.1 M sodium carbonate/bicarbonate buffer, pH 10.0. Slowly add 0.1 ml of vinyl sulfone and stir the mixture overnight at room temperature. Dialyse the activated protein against 0.15 M sodium chloride for 6 hours at room temperature.
2. Add 1.5 mg of 5-pentylresorcinol in 0.2 ml iso-propanol and incubate the mixture overnight at room temperature.
3. Dialyse the conjugate for 3 days versus PBS/azide with 3 changes of 2 liters each.
4. Determine the protein concentration was using the Lowry protein assay and the dilute to 1 mg/ml. Store aliquots at −20° C.

Figure 4:
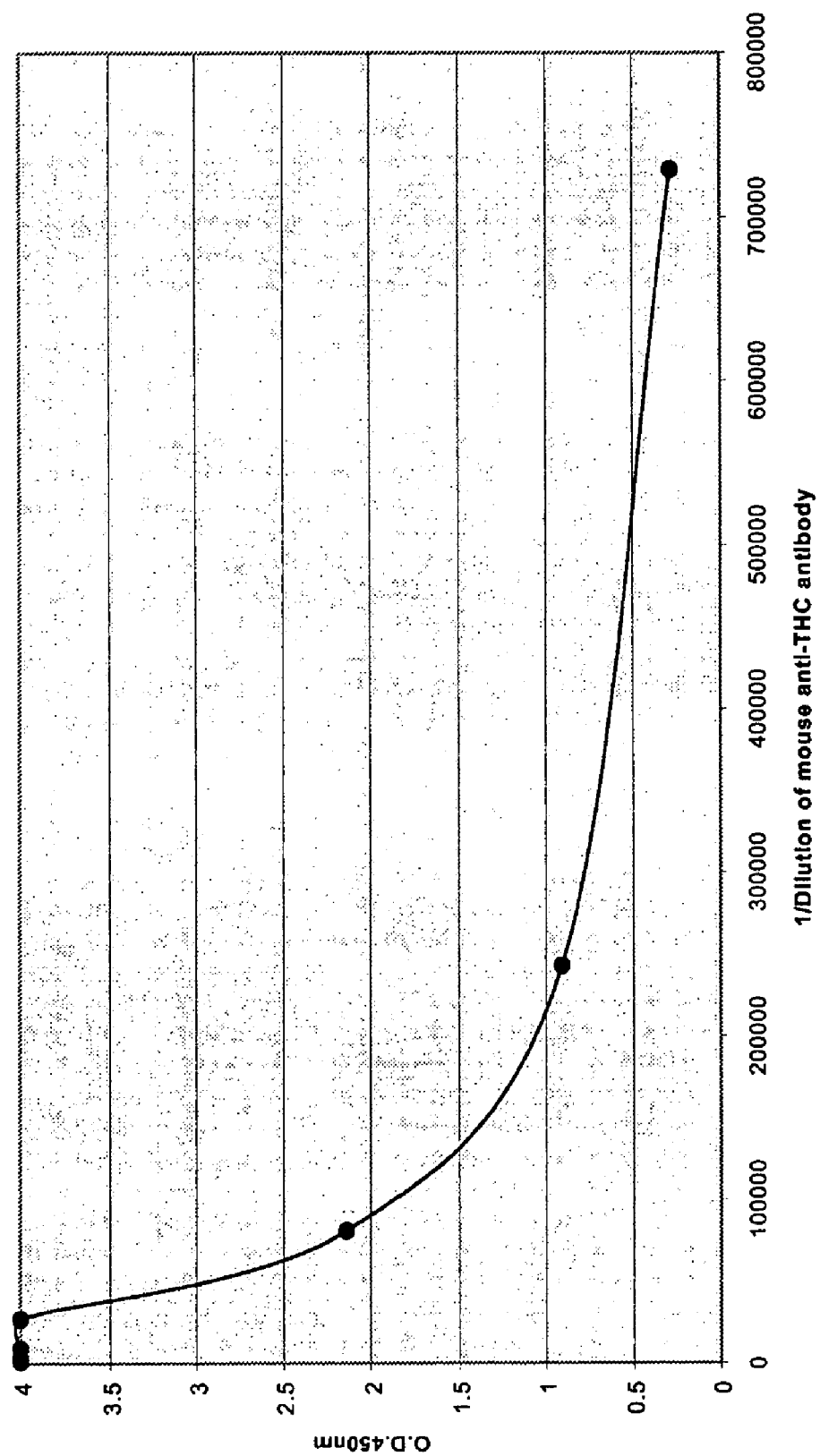
FIG. 4: titration curve for binding of anti-THC antibody to immobilised 5-pentylresorcinol/BSA conjugate (BSA-CAN).

BSA-CAN conjugates were also tested by enzyme immunoassay as described for the BSA-THC conjugate. FIG. 4 shows a typical titration profile.

III. Lateral Flow Immunochromatography Test for *Cannabis*

Figure 5:
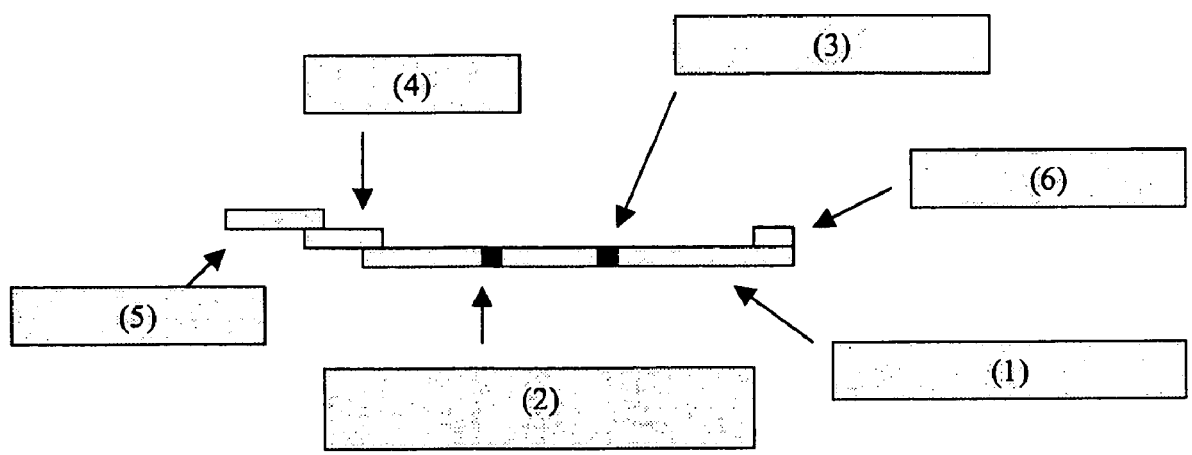
FIG. 5: Diagram illustrating a lateral flow test strip for use in carrying out a lateral flow immunochromatography test according to the invention in which (1) is a porous test strip of nitrocellulose sheet laminated onto a backing support, (2) is the analyte detection zone presenting immobilised BSA-CAN, (3) is the control zone presenting immobilised antibody to capture labelled antibody, (4) is a label release pad which releases labelled antibody into liquid drawn into this pad from the sample receiving pad (5) and (6) is a wicking pad.

BSA-THC and BSA-CAN were used to set up a lateral flow test for *cannabis*. FIG. 5 shows the format of this test. The conjugates were diluted 1 mg/ml in PBS containing 3% ethanol. BSA-THC or BSA-CAN were immobilised on nitrocellulose strips using inkjet or direct contact methods. Sheep anti-mouse IgG antibodies (acting as control line (3)) at 0.5 mg/ml were also immobilised on the nitrocellulose strip (2). The strips were dried overnight at 37° C. A glass fibre pad (4) containing gold-labelled mouse monoclonal anti-THC antibody (unlabelled antibody obtained from East Coast Biologics, USA) a sample pad (5) and a wicking pad (6) were laminated onto the nitrocellulose strip as shown in FIG. 5. Oral fluid samples (1 ml) were collected using a Cozart sample collection pad (Product No. MANU018) and diluted with 2 ml of Cozart oral fluid dilution buffer (Product No. CR-BUFF). 120 µl of the diluted oral fluid were added slowly to the sample pad. The liquid moved across the strip by capillary action hydrating the gold-labelled antibody.

If the sample contained no *cannabis*, the labelled antibody bound to the immobilised BSA-drug conjugate giving a reddish/brown line. The control line captured excess labelled antibody. If the diluted oral fluid sample contained *cannabis*, this bound to the gold-labelled antibody in preference to the immobilised BSA-drug conjugate resulting in reduced colour intensity of the BSA-drug line. The result of each test was read using the Cozart® Rapiscan reader (GB Patent no. 2339615, corresponding published International Patent Application WO 00/04831 and Journal of Forensic Science 2001, volume 46, pages 1214-1220, Product No. CR200S-UK). The reader measures colour intensity of the BSA-drug line, which is inversely related to the concentration of the drug in the diluted oral fluid sample, and reports the result of the test as positive or negative against a pre-set cut off value. Drug-free oral fluid was spiked with THC (I) or THC-COOH (II) or THC-OH (III) at various concentrations and then tested using the BSA-THC or BSA-CAN lateral flow strips. The lowest concentrations of drugs giving a positive signal on the reader are listed in Table 1. It is clear that using the novel BSA-CAN conjugate increased the sensitivity of detection of THC by about 10-fold.

TABLE 1

| Immobilised Conjugate | Compound tested | Concentration [ng/ml] giving positive Cozart ® Rapiscan Response |
|---|---|---|
| BSA-THC | THC | 200 |
| | THC—COOH | 10 |
| | THC—OH | 200 |
| BSA-CAN | THC | 20 |
| | THC—COOH | 1.0 |
| | THC—OH | 20 |

The invention claimed is:

1. A method for detecting in a liquid sample delta-9-tetrahydrocannabinol (THC) or one or more of THC and its metabolites 11-nor-9-carboxy-delta-9-THC (THC-COOH) and 11-hydroxy-delta-9-THC (THC-OH), which comprises:

(a) contacting said sample with (i) a 5-pentylresorcinol/macromolecular carrier conjugate wherein 5-pentylresorcinol is conjugated via a hydroxyl group or a derivative thereof on its benzene ring to the carrier and (ii) an antibody capable of binding both THC and said conjugate; and (b) determining whether binding of said antibody to said conjugate is reduced in the presence of said sample, wherein said antibody may exhibit cross-reactivity with said metabolites and reduction of the binding of said antibody to said conjugate is indicative of the presence of THC or the presence of one or more of THC, THC-COOH and THC-OH.

2. The method as claimed in claim 1 wherein said antibody is capable of binding all of delta-9 tetrahydrocannabinol (THC), 11-nor-9-carboxy-delta-9-THC (THC-COOH) and 11-hydroxy-delta-9-THC (THC-OH), whereby one or more of THC, THC-COOH and THC-OH may be detected in the liquid sample.

3. The method as claimed in claim 2 wherein said antibody is an antibody raised to THC-COOH coupled to a carrier protein via its carboxylate group.

4. The method as claimed in claim 1 wherein the carrier of said 5-pentylresorcinol/carrier conjugate is a protein.

5. The method as claimed in claim 4 wherein said protein is selected from the group consisting of bovine serum albumin, horseradish peroxidase, ovalbumin, a gamma globulin, and thyroglobulin.

6. The method as claimed claim 1 wherein said antibody is labeled directly or indirectly.

7. The method of claim 1, wherein said 5-pentylresorcinol conjugate is labeled directly or indirectly or the carrier of said conjugate also serves as a detectable label.

8. The method of claim 1, wherein said conjugate is a conjugate obtained by coupling 5-pentylresorcinol via its hydroxyl groups to amino groups of said carrier using dimethyl aminopyridine/disuccinimidyl carbonate or vinyl sulfone.

9. The method of claim 1, wherein 5-pentylresorcinol is coupled to said carrier via a spacer molecule.

10. The method of claim 1, wherein one of said antibody and said 5-pentylresorcinol/carrier conjugate is immobilised on a solid support.

11. The method of claim 10, wherein the solid support is used in a lateral flow chromatography assay.

12. The method of claim 11, wherein said 5-pentylresorcinol conjugate is immobilised in an analyte detection zone on a test strip or sheet and said antibody is labeled.

13. The method of claim 12, wherein said antibody is gold particle labeled.

14. The method of claim 1, wherein said liquid sample is derived from, urine, blood, sweat, ocular fluid, saliva, or hair.

15. The method of claim 12, wherein the sample applied to the test strip or sheet is buffered-diluted oral fluid.

16. A test strip or sheet for use in a lateral flow analytical device for a carrying out a lateral flow immunochromatography assay, said test strip or sheet comprising:
  (i) a strip or sheet comprising a dry porous material having immobilised thereon in an analyte detection zone (a) a 5-pentylresorcinol/macromolecular carrier conjugate wherein 5-pentylresorcinol is conjugated via a hydroxyl group or a derivative thereof on its benzene ring to the carrier, or (b) an antibody capable of binding both THC and said conjugate; and
  (ii) joined to, or integral to, said strip or sheet providing said analyte detection zone, a label release zone containing either said antibody in labeled form, if said analyte detection zone presents immobilized 5-pentylresorcinol/carrier conjugate, or, if said analyte detection zone presents immobilized antibody, detectable 5-pentylresorcinol conjugate, whereby said labeled antibody or detectable conjugate will be released into a liquid sample drawn into the label release zone.

17. The test strip or sheet according to claim 16 wherein said dry porous material is nitrocellulose.

18. The test strip or sheet according to claim 16 wherein 5-pentylresorcinol conjugate is immobilised in an analyte detection zone.

19. The test strip or sheet of claims 16, which further comprises a control zone which is located distal to said analyte detection zone in the direction of intended liquid flow.

20. The test strip or sheet of claim 16, which further comprises a sample receiving member or pad proximal to said label release zone having regard to the intended direction of liquid flow.

21. The test strip or sheet of claim 16, which further comprises an absorbent waste pad distal to said analyte detection zone in the direction of intended liquid flow.

22. The test strip or sheet of claim 16, wherein the strip or sheet is inserted into a housing.

23. A lateral flow device, comprising a test strip or sheet, wherein said test strip or sheet comprises:
  (i) a strip or sheet comprising a dry porous material having immobilized thereon in an analyte detection zone (a) a 5-pentylresorcinol/macromolecular carrier conjugate wherein 5-pentylresorcinol is conjugated via a hydroxyl group or a derivative thereof on its benzene ring to the carrier, or (b) an antibody capable of binding both THC and said conjugate; and
  (ii) joined to, or integral to, said strip or sheet providing said analyte detection zone, a label release zone containing either said antibody in labeled form, if said analyte detection zone presents immobilized 5-pentylresorcinol/carrier conjugate, or, if said analyte detection zone presents immobilized antibody, detectable 5-pentylresorcinol conjugate, whereby said labeled antibody or detectable conjugate will be released into a liquid sample drawn into the label release zone.

24. A kit comprising:
  (a) a 5-pentylresorcinol/macromolecular carrier conjugate wherein 5-pentylresorcinol is conjugated via a hydroxyl group or a derivative thereof on its benzene ring to the carrier; and
  (b) an antibody capable of binding both THC and said conjugate.

25. The kit as claimed in claim 24 wherein a direct label or secondary labeled antibody is provided for labeling said antibody.

26. The kit as claimed in claim 24 wherein said conjugate is a detectable conjugate.

27. The kit as claimed in claim 24, wherein said antibody or said conjugate is immobilised on a solid support.

28. The kit as claimed in claim 27, wherein the solid support is used in a lateral flow chromatography assay.

* * * * *